United States Patent [19]

Buchanan et al.

[11] Patent Number: 5,465,536
[45] Date of Patent: Nov. 14, 1995

[54] CONTAINMENT OF HEAVY VAPOR CLOUDS AND AEROSOLS

[75] Inventors: John S. Buchanan, Hamilton; Frederick J. Krambeck, Cherry Hill; Klaus W. Schatz, lawrenceville, all of N.J.

[73] Assignee: Mobil Oil Corporation, Fairfax, Va.

[21] Appl. No.: 187,936

[22] Filed: Jan. 27, 1994

Related U.S. Application Data

[63] Continuation-in-part of Ser. No. 133,402, Oct. 8, 1993, Pat. No. 5,362,446, which is a continuation-in-part of Ser. No. 950,354, Sep. 24, 1992, Pat. No. 5,286,456.

[51] Int. Cl.⁶ .................................................. E04H 5/02
[52] U.S. Cl. ........................... 52/198; 454/49; 454/339; 588/249; 588/259
[58] Field of Search .................. 588/249, 259; 454/54, 55, 49, 250, 339; 52/198

[56] References Cited

U.S. PATENT DOCUMENTS

| | | |
|---|---|---|
| 388,260 | 8/1888 | Carey . |
| 425,369 | 4/1890 | Cowell . |
| 1,259,914 | 3/1918 | Seward et al. ............... 454/339 X |
| 1,408,432 | 3/1922 | Arnold ........................ 52/198 X |
| 1,438,199 | 12/1922 | Voges . |
| 2,097,953 | 11/1937 | Ludwig ....................... 454/55 X |
| 2,180,586 | 12/1937 | Gustafsson ................. 454/55 X |
| 2,259,626 | 10/1941 | Erikson ...................... 454/55 |
| 2,699,960 | 1/1955 | Callery et al. . |
| 2,796,297 | 6/1957 | Klock . |
| 3,716,343 | 2/1973 | Chapman . |
| 3,795,712 | 3/1974 | Torck et al. . |
| 4,210,460 | 7/1980 | Seidenberger . |
| 4,273,285 | 6/1981 | Scholbrock . |
| 4,472,268 | 9/1984 | Olah . |
| 4,552,624 | 11/1985 | Clarkson . |
| 4,608,064 | 8/1986 | Napadow .................... 454/54 X |
| 4,938,935 | 7/1990 | Audeh et al. . |
| 4,938,936 | 7/1990 | Yan . |
| 4,939,833 | 7/1990 | Thomas . |
| 5,041,146 | 8/1991 | Simmerlein-Erlbacher . |
| 5,073,674 | 12/1991 | Olah . |
| 5,098,668 | 3/1992 | Callen et al. . |
| 5,254,798 | 10/1993 | Zoback ...................... 588/249 X |
| 5,277,881 | 1/1994 | Partridge, Jr. et al. . |

FOREIGN PATENT DOCUMENTS

| 243923 | 7/1985 | German Dem. Rep. . |
| 271322 | 5/1988 | German Dem. Rep. . |

OTHER PUBLICATIONS

Hazardous Material Spills, Conference, 1988, E. C. Norman, pp. 363 to 365.
Kirk–Othmer Encyclopia of Chemical Technology, 3rd Ed, vol. 1, pp. 624, 654 to 655.
Gordon K. Braley, Several Remedies for the Treatment of Spillages of Liquid Hazardous Chemicals, pp. 103 to 108.
Mitigation of Aerosol Releases, Hans K. Fauske, Presentation to HF User Group, Amoco Corp., Chicago Ill., Mar. 25, 1988, 13 pages.
Aersol Reduction from Episodic Releases of Anhydrous HF Acid by Modifying the Acid Catalyst with Liquid Onium, Comey et al., Presentation of AIChE 1993, Summer meeting, Aug. 16, 1993, pp. 1–17.

Primary Examiner—Carl D. Friedman
Assistant Examiner—Christopher Todd Kent
Attorney, Agent, or Firm—Alexander J. McKillop; Dennis P. Santini; Gerald L. Harris

[57] ABSTRACT

A system for containment of heavy vapor cloud and aerosol from a potential source of hazardous vapor comprising walled surfaces surrounding the vapor source and a roof above the vapor source and forming with the walled surfaces an enclosure for the vapor source. The roof is porous with openings therethrough dimensioned for minimizing wind shear and extending over at least about 20% of the surface area of the roof, and a device is located within the enclosure for absorbing the vapor.

20 Claims, 3 Drawing Sheets

CONTAINMENT OF HEAVY VAPOR CLOUDS AND AEROSOLS

CROSS-REFERENCE TO RELATED APPLICATIONS

This application is a continuation-in-part of both (1) application Ser. No. 07/950,354, filed Sep. 24, 1992, now U.S. Pat. No. 5,286,456, and (2) application Ser. No. 08/133,402, filed Oct. 8, 1993, now U.S. Pat. No. 5,362,446, which is a continuation-in-part and division of said application Ser. No. 07/950,354.

BACKGROUND OF THE INVENTION

1. Field of the Invention

The present invention relates to a method and a system for containing and neutralizing a heavy vapor cloud and aerosols of corrosive and toxic substances, such as hydrogen fluoride (HF), hydrofluoric acid, ammonia, chlorine and the like. More particularly, the present invention relates to a method and system for containing and neutralizing such substances in the event of an accidental release.

2. Description of Prior Art

Hydrofluoric acid is toxic and corrosive. In gaseous vapor or liquid form, hydrofluoric acid attacks the skin, and will on contact cause ulceration of mucous membranes and possibly chemical pneumonia to those exposed to it. Hydrofluoric acid is, however, an industrially important chemical. It is used to manufacture fluorine and to prepare fluorides and other chemical compounds. It is also used as a catalyst for isomerization, condensation, polymerization and hydrolysis reactions. The petroleum industry uses anhydrous hydrogen fluoride primarily as a liquid catalyst for the alkylation of olefinic hydrocarbons to produce alkylate for increasing the octane number of gasoline.

The petroleum refining industry has always recognized the potential for hazard created by HF alkylation units. Accordingly, the industry has consistently ensured that a high level of safety is maintained by use of superior mechanical and metallurgical specifications, and operational practices in the design, construction and operation of these units. As a result, the HF alkylation process has enjoyed an almost unparalleled record of industrial safety. However, the industry has continued to seek enhancement of the intrinsic safety of these units to secure a higher level of potential operating safety and to guard against the consequences of an uncontrolled release of unit contents.

The potential magnitude of the risk inherent in operating an HF alkylation unit may be reduced by a number of qualitative methods that have been proposed for treating HF spills. The most common method is the use of a simple water drench system. Kirk-Othmer Encyclopedia of Chemical Technology, 3rd Edition, Volume 1, page 655 reports that water the most common absorption liquid is used for removing acidic gases, especially if the last contact is with water of alkaline pH. However, because of the aerosol nature of an HF cloud in which the HF droplets are in the order of 0.1 micron and thus very small compared to droplets of water in a simple water drench, the water drench generally has difficulty in removing all the HF present in the cloud.

U.S. Pat. No. 4,210,460 relates to treating an HF liquid spill by applying to the spill a quantity of an aqueous solution of calcium acetate equal to at least seven times the estimated volume of the spill, and thereafter treating the spill with powdered magnesium oxide. The mixture is tested using a pH indicator such as bromothymol blue. After the mixture reaches a persistent blue color, indicating a safe state, the spill is cleaned up mechanically.

At the 1982 Hazardous Material Spills Conference, Edward C. Norman of National Foam System Inc reported the application of limestone and then CHF-784 foam (a proprietary composition) to the contents of a damaged tank emitting an HF cloud. An immediate reduction in fume evolution was apparent after the foam application.

Gordon K. Braley, at the proceedings of the 1980 National Conference on Control of Hazardous Material Spills, in Louisville, Ky. on May 15, 1980 reported the treatment of relatively small amounts of controlled liquid spills of anhydrous hydrogen fluoride with high molecular weight polymers including polyacrylamide, polymethyl methacrylate, and polyvinyl alcohol. These materials applied in the form of a bead polymer formed a skin over the spill preventing fuming of the liquid. Polyacrylamide was deemed the most effective skin-forming agent.

SUMMARY OF THE INVENTION

The present invention provides an effective method and system for containing and neutralizing heavy vapor clouds and aerosols. In accordance with a broad aspect of the present invention there is provided a system and for containment of heavy vapor cloud and aerosol from a potential source of hazardous vapor comprising walled surfaces surrounding the vapor source and a roof above the vapor source and forming with the walled surfaces an enclosure for the vapor source. The roof is porous with openings therethrough dimensioned for minimizing wind shear and extending over at least about 20% of the surface area of the roof, and means for absorbing the vapor is located within the enclosure.

In accordance with another broad aspect of the invention there is provided a method for containment of heavy vapor cloud and aerosol from a potential source of hazardous vapor comprising the steps of surrounding the vapor source with walled surfaces, and positioning a roof above the vapor source to form with the walled surfaces an enclosure for the vapor source. The roof is porous with openings therethrough dimensioned for minimizing wind shear, and extending over at least about 20% of the surface area of the roof. The method additional includes locating means for absorbing the vapor within said enclosure.

Thus, in accordance with the present invention, a potential source of hazardous vapors, such as an HF alkylation unit, is surrounded by a high wall which is substantially impermeable to the vapors. A horizontal, porous roof covers the area enclosed by the wall to reduce the effects of wind while avoiding the difficulties associated with a hermetically sealed enclosure. Means for absorbing the hazardous vapors are provided within the enclosure.

In accordance with a specific aspect of the invention, vapor absorbing means is provided by an intake of at least one absorption tower located within the enclosed and covered area. Vapors released by the source are taken into the tower and absorbed by a liquid spray therein. In another embodiment, liquid or powder sprays within the enclosure are used to absorb vapors. Stationary porous solids-based sorbent devices are also contemplated.

One method of mitigating the effects of an accidental release of a hazardous vapor or aerosol, such as hydrofluoric acid, is to surround the source with spray nozzles of an absorbing liquid, such as water. In the event of an emergency, this system is actuated to maintain a spray curtain, which will absorb a large portion of the released material in the enclosure.

Absorbing means also include a counter-current absorption tower, containing packing or multiple trays, which provide effective contact between a gas and a liquid sorbent. Problems of detection and decision that may arise can be avoided by maintaining the tower in continuous operation. This can be implemented by positioning one or more water cooling towers next to the potential vapor source. Also, it is possible to provide some absorption tower capacity next to the potential vapor source which does not operate continuously, but which can be turned on in the event of an emergency. However, this is less preferred than either a continuously operating tower or a water spray system.

DESCRIPTION OF SPECIFIC EMBODIMENTS

Figure 1:
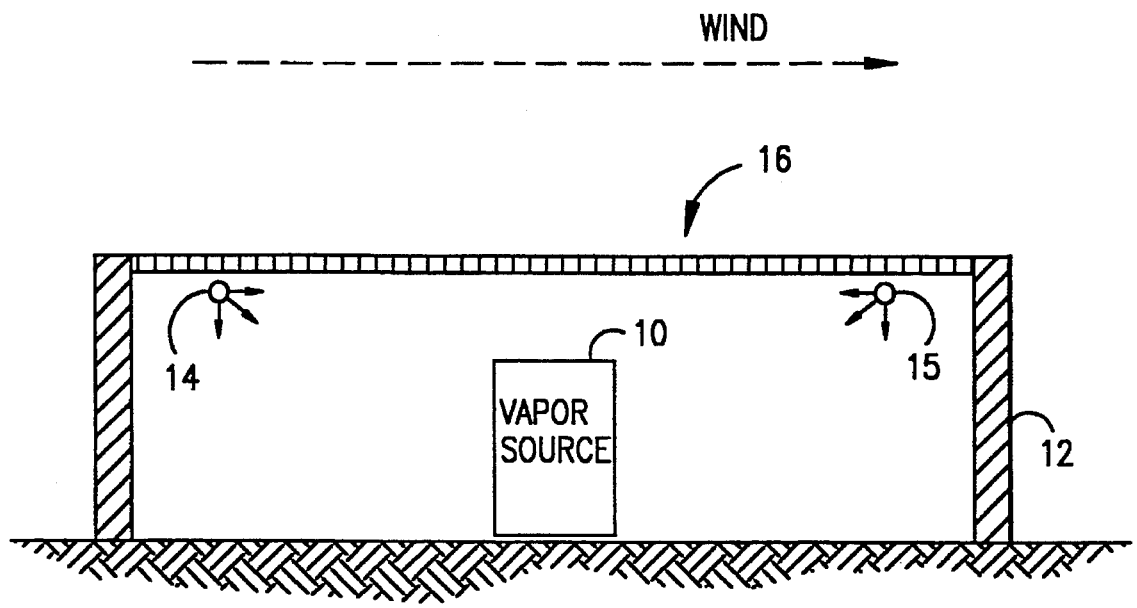
FIG. 1 is a schematic cross-sectional view of an embodiment of the present invention wherein a vapor source is enclosed by walled surfaces and a porous roof, and spray nozzles are provided to absorb the vapor.

A critical concern is ensuring that essentially all hazardous vapors which are released by a source as an HF alkylation unit are entrained into vapor absorbing means such as an absorption tower. It is difficult to closely surround every component in a chemical processing unit with fans and duct work to suck in leaking vapors. As a practical matter, an absorption tower and its intake will generally have to be located some distance from the potential source of hazardous material. The local wind velocity then has a major bearing on the efficiency of entrainment.

Similarly, the effectiveness of a water or powder spray system is affected by the wind, since a high wind can more quickly blow the hazardous vapors past or through the spray curtains. The acceptable response time for actuating a spray mitigation system is also shortened as wind velocity increases. For stationary solid sorbents, confining the vapors in their vicinity will increase their collection efficiency.

Example 1

As an example, consider a 1000 cubic ft vessel filled with a hazardous gas at 20 atmospheres, which develops a leak such that the contents are discharged at a constant rate over five minutes. For an ideal gas and constant temperature, this translates to a hazardous gas flow rate of about 67 cu/ft/sec which would have to be taken into the base of an adsorption tower by an intake fan, in the absence of wind effects.

Example 2

Assume an absorption tower is located 80 ft away from a source of hazardous vapor, with a 20 mi/hr wind blowing directly towards the absorption tower. Because of turbulent mixing effects, the cross-sectional area of air flow which is contaminated with hazardous vapor may be about 20 ft high and 40 ft wide, or 800 sq ft, when the air flow reaches the absorption tower. The intake to the absorption tower is 40 feet wide and its base is located at ground level. At a wind speed of 20 mi/hr (29.3 ft per second), this requires 23,440 cu/ft/sec of contaminated air to be taken into the tower for scrubbing. This is about 350 times the volumetric flow of the vapor alone, from Example 1. Thus, the higher air flow places a much greater demand on the air handling section of the absorber and reduces absorption efficiency. Also, because the vapor concentration is reduced by dilution with air, the effectiveness of absorption would be substantially reduced.

Example 3

In this case, the source and absorption tower are as described in Example 2, except the wind is not blowing directly towards the absorption tower. Then the tower would have little effect unless inlet ducts were located downwind of the leak. If the wind direction is almost directly towards the tower, increasing the tower intake flow rate can help alter the air flow streamlines to direct the bulk of the contaminated air into the tower. In general, however, the effect of the wind will be to blow the contaminated air past or away from the absorption tower.

Example 4

The source is as described in Example 1, but the vapor absorbing means is a liquid or powder spray curtain. In this instance, wind tends to blow any released vapor past the spray curtain, thereby reducing its effectiveness.

Example 5

In this example, the source and spray curtain are as described in Example 4, except they are enclosed within a wall which is substantially impermeable to gas flow. The wall breaks the direct force of the wind. However, the wind shear over the enclosed area sets up vertical eddies which tend to mix the air in the enclosed area with the ambient air flow, and thereby facilitate escape from the enclosure.

With reference to FIG. 1, one embodiment of the present invention includes a source of hazardous vapor 10, a wall 12 surrounding the source 10 and a spray curtain 14,15 as described in Example 5. However, the enclosed area is covered with a porous cover 16, which substantially reduces the generation of large-scale eddies within the enclosure by interrupting the transmission of momentum from the ambient air to the air inside the enclosure. The enclosure defined by the wall 12 and the cover 16 increases the residence time in the vicinity of the spray, and reduces dilution by the ambient air, both of which increase the effectiveness of the spray. Since a vapor release is initially contained within the enclosure, this increases the window of response time to a release. Also, a small leak from the source 10 can be more readily detected within the confines of the enclosure, because the vapor will build up in the enclosure.

Figure 2:
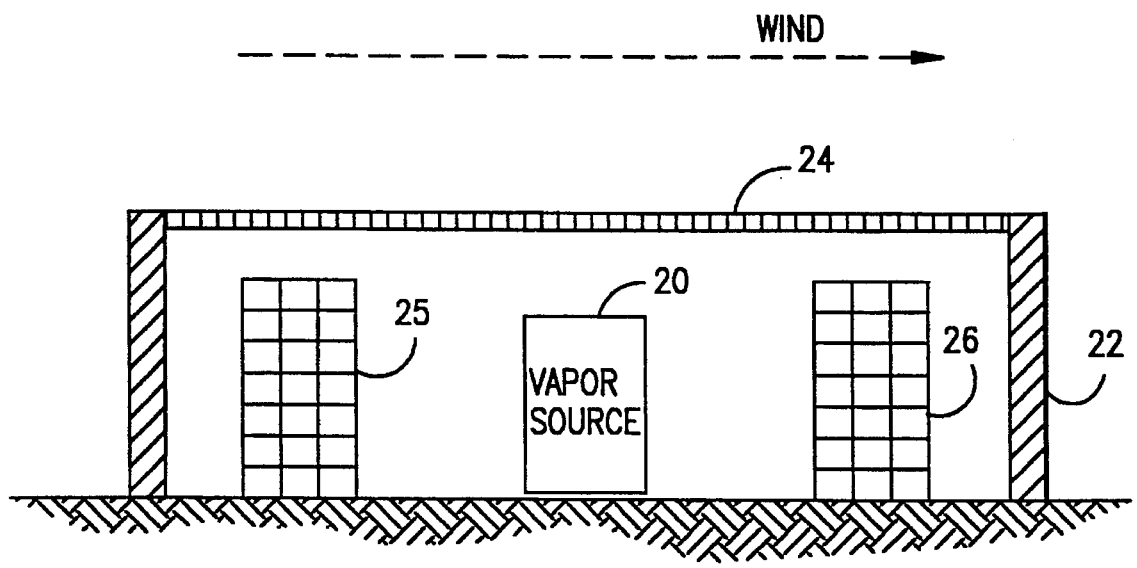
FIG. 2 is a schematic cross-sectional view of another embodiment having the enclosure of FIG. 1, but with wall surfaces for absorbing the vapor.

In the embodiment of FIG. 2, the vapor source 20, wall 22 and roof 24 are as described in FIG. 1. However, the primary means of sorption is a plurality of stationary structures 25,26 with exposed surfaces consisting of solid or semi-solid material, e.g. a gel, which will absorb the hazardous vapor. The surfaces are impregnated with vapor absorbing dry powders such as metal oxides, e.g. titanium oxide ($TiO_2$), alumina ($Al_2O_3$), calcium oxide (CaO), or with metal carbonates like lime stone powder ($CaCo_3$), sodium bicarbonate ($NaHCO_3$), or with metal hydroxides like calcium hydroxide ($Ca(OH)_2$).

The FIG. 2 system has the merit of being a totally passive system, so it will be effective without reliance on procedures for detecting leaks and actuating emergency response systems.

Figure 3:
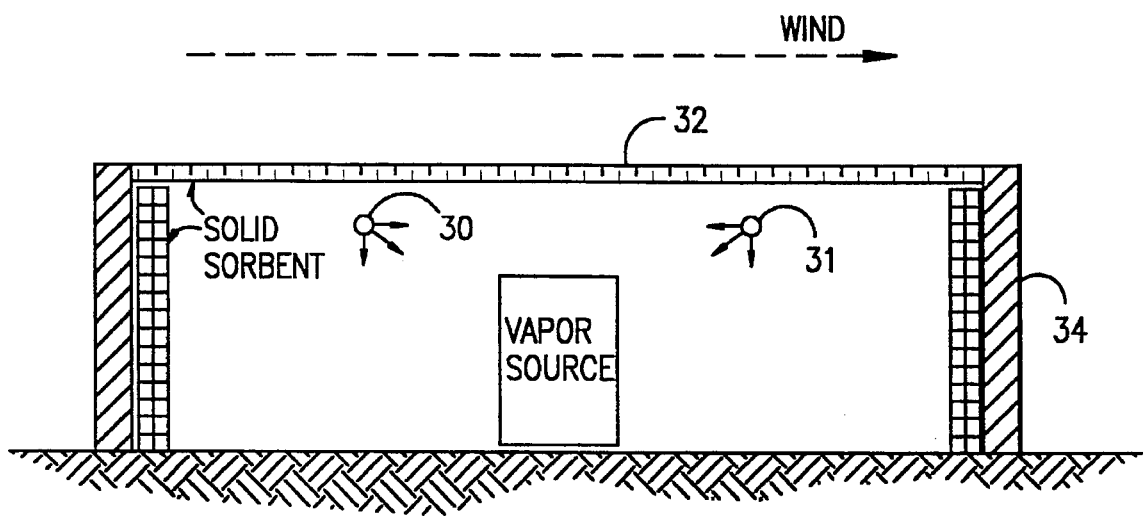
FIG. 3 is a schematic cross-sectional view of another embodiment having the enclosure of FIG. 1, but with absorbing wall surfaces and an absorbing spray.

Two or more vapor absorbing means may be advantageously combined as shown in FIG. 3 where, the primary means of sorption of hazardous vapors is a liquid or powder spray curtain 30,31. The spray curtain, e.g. water, captures 80–90% of the released vapor, so much less stationary solid sorbent is required. The solid sorbent is coated in openings in the porous cover 32, as well as along the wall 34 of the enclosure.

Figure 4:
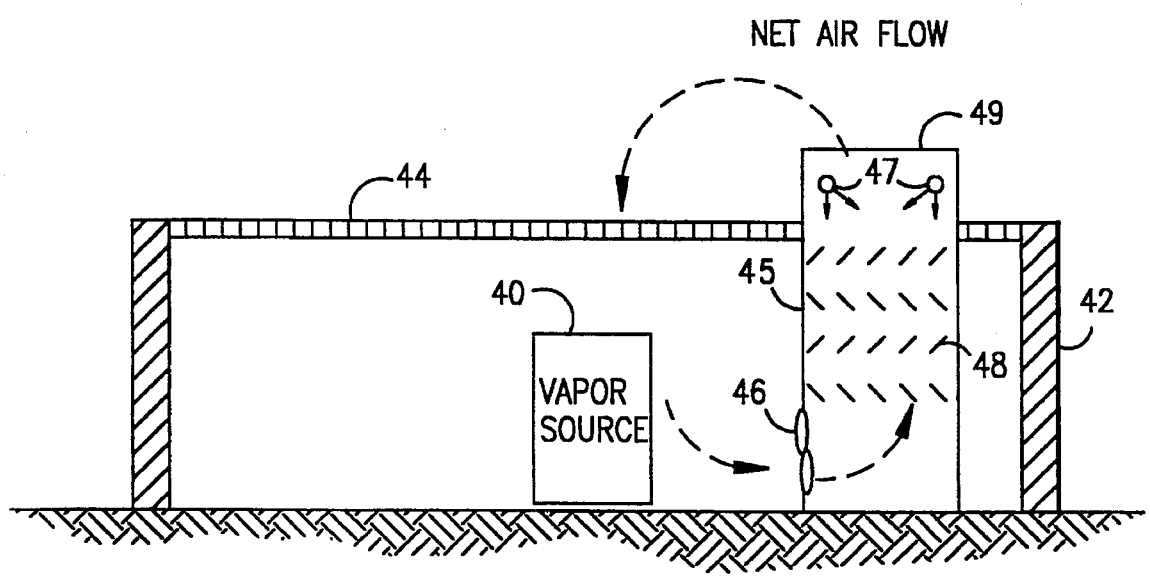
FIG. 4 is a schematic cross-sectional view of another embodiment having an enclosure similar to that of FIG. 1, but with a tower extending through the roof for absorbing vapor.

With reference to FIG. 4, another embodiment of the invention has the source 40, wall 42, and porous cover 44 as described with reference to FIG. 1, but the means for absorbing vapor is an absorption tower 45 with forced-draft intake 46, a liquid spray 47 from within the top of the tower 45, and internal baffles 48, packing or trays to enhance contacting efficiency. The surfaces of the baffles may be coated or impregnated with the vapor absorbing dry powders described hereinabove with reference to FIG. 2. The tower is preferably operated continuously, although a specially-designed scrubber which can quickly be swung into operation would also be useful. Preferably, the top of the tower 49 protrudes above the porous cover 44, creating a net downflow through the porous cover 44, to help retain vapors in the enclosure until they are drawn into the tower 45 for sorption.

Maintaining a high degree of porosity in the vertical direction of the roof, preferably greater than about 20% with respect to light, air, and atmospheric precipitation provides a relatively normal atmosphere in the enclosure.

Figure 5:
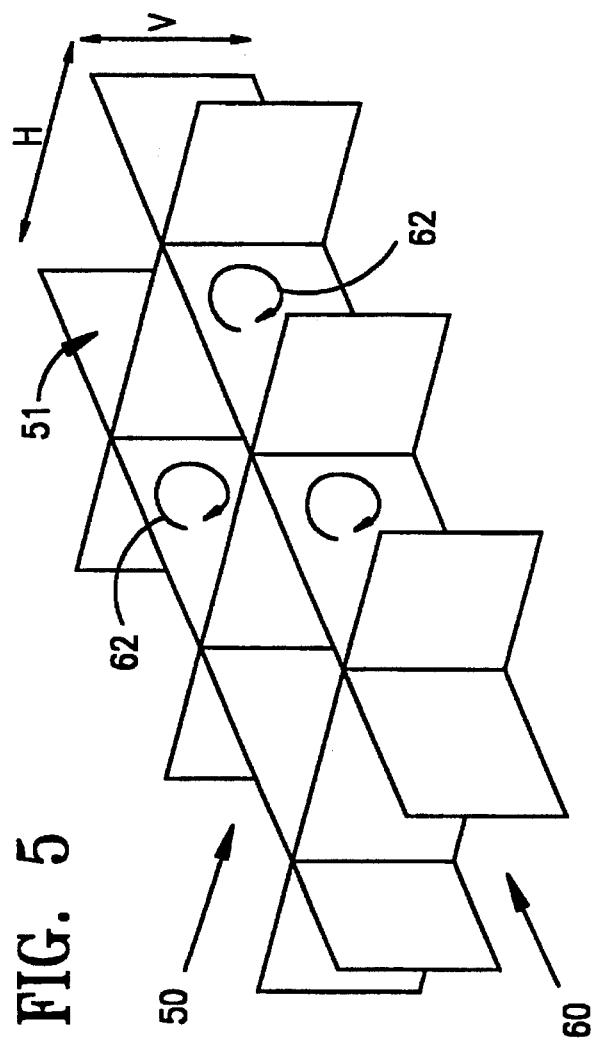
FIG. 5 is an embodiment of a roof for the enclosures of the present invention.
Figure 6:
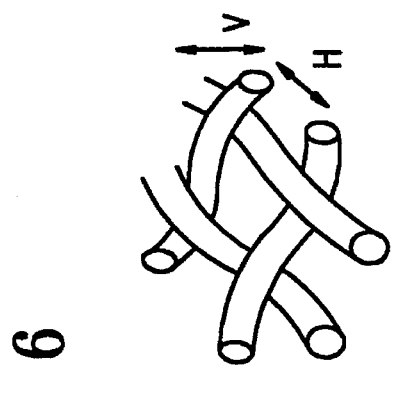
FIG. 6 is another embodiment of a roof for the enclosures of the present invention.

The following aspects of the invention permit the porous cover to be most effective as a barrier to air exchange which might be induced by wind shear. With reference to FIG. 5, for a covering 50 with openings or channels 51 constituting greater than 40% of the surface area, the ratio of the horizontal width (H) of the openings in the covering to the vertical depth (V) of the openings is preferably less than 6:1, and more preferably less than 3:1. The ratio (H/V) for the vertical channels 51 of FIG. 5 is about 1. However, for a covering made of netting as shown in FIG. 6 the ratio may be about 2. For a thin metal or polymer plate with large holes in it, this ratio may be greater than 6, but it is then preferred to have the combined area of the holes be less than 40% of the total surface area, in order to minimize the effects of wind shear. If the openings in the covering are not square, e.g. rectangular, circular or irregular, the horizontal width is determined by the square root of the horizontal area of the opening.

Thus, the invention seeks to mitigate the effect to the wind shear across the covering of the enclosure.

The solution in accordance with the present invention is to have the porous covering but with a sufficient vertical surface to prevent the main flow of the wind, as shown by the arrow 60, from establishing large circulation patterns through the openings. However, is acceptable to have small circulation patterns 62 within the openings that minimize wind penetration of the covering. If the openings are too short vertically, it is believed that wind shear would be reduced to some extent but with diminishing effectiveness. It is preferred that the ratio (H/V) be less than 6:1 to confine recirculation within the openings. If the ratio is greater than 6:1 there may be some recirculation along with some penetration of the overall wind shear effect.

Figure 7:
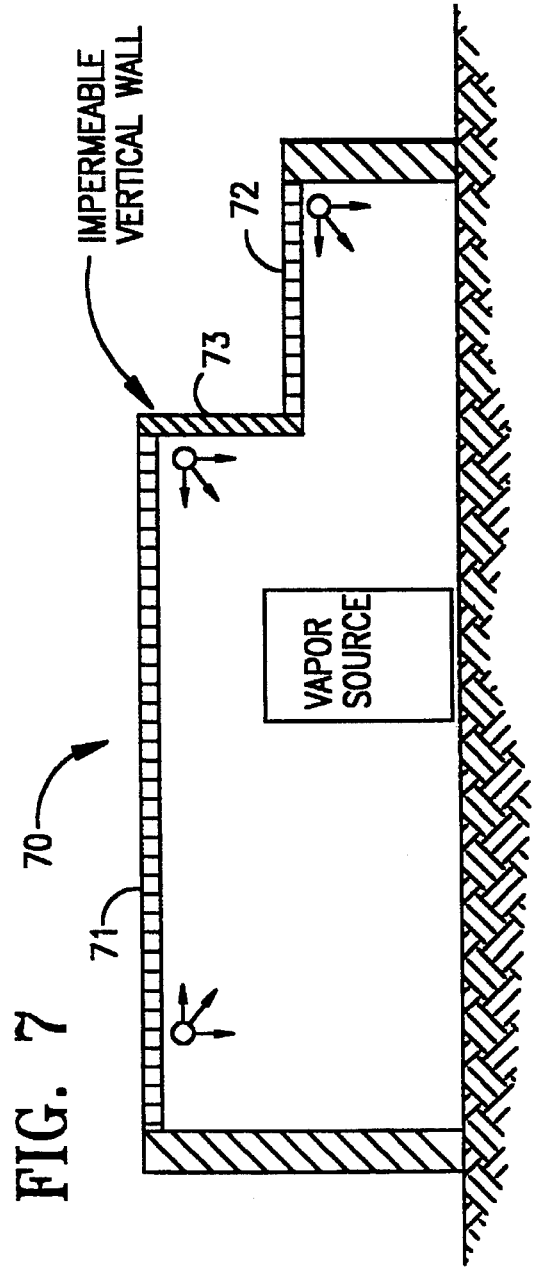
FIG. 7 is a schematic cross-sectional view of another embodiment showing a two tier roof.

The upper surface of the covering is maintained substantially horizontal. With reference to FIG. 7, if the entire covering 70 of the enclosure cannot be maintained in one horizontal plane, it is preferred to arrange the covering surface in two or more horizontal steps 71,72, joined by one or more substantially impermeable vertical walls 73.

The present invention contemplates the use of an impact plate and meshed pad disclosed in U.S. patent application Ser. No. 07/950,354, filed Sep. 9, 1992 now U.S. Pat. No. 5,286,456, which application is incorporated herein by reference. The impact plate and meshed pad may be used on any interior wall surface facing the vapor source. The application relates to a system for containing and neutralizing a liquid jet of an aerosolable, corrosive and toxic substance such as hydrogen fluoride, hydrofluoric acid, ammonia, chlorine and the like before the jet can form a corrosive and toxic cloud. The system provides for increasing rainout from a jet exiting a pressurized source and thereby substantially minimizes the opportunity for formation of a corrosive and toxic cloud. An impact plate is spaced from the pressurized source for deflecting the liquid jet to dissipate its forward velocity and energy. A meshed pad is positioned in abutting engagement with the impact plate and facing the source for initially reducing the velocity and energy of the liquid jet, and for preventing back and radial splash of the liquid jet deflecting off the impact plate to coalesce droplets of the substance and thereby produce a collectable run-off. The impact plate and meshed pad are positioned a distance from the source to impact the liquid jet before the liquid jet is capable of expanding to form a substantial aerosol of vaporized substance.

While the invention has been described in conjunction with specific embodiments thereof, it is evident that many alternatives, modifications, and variations will be apparent to those skilled in the art in light of the foregoing description. Accordingly, it is intended to embrace all such alternatives, modification, and variations as fall within the spirit and broad scope of the appended claims.

What is claimed:

1. A system for containment of heavy vapor cloud and aerosol from a potential source of hazardous vapor comprising:

a potential hazardous vapor source; walled surfaces surrounding said vapor source;

a roof above said vapor source and forming with said walled surfaces an enclosure for said vapor source, said roof being porous with openings therethrough extending over at least about 20% of the surface area of said roof to provide access for ambient light, air and precipitation, said openings being dimensioned for minimizing wind shear and resultant wind shear eddies within said enclosure by interrupting transmission of momentum from ambient air to air within said enclosure, and means within said enclosure for absorbing said vapor;

whereby said roof increases residence time of said vapor with said absorbing means.

2. The system of claim 1 wherein said openings in said roof are greater than about 40% of the surface area of said roof; and said openings have a horizontal width to depth ratio of less than about 6:1.

3. The system of claim 2 wherein said horizontal width to depth ratio of said openings is less than about 3:1.

4. The system of claim 1 wherein said openings in said roof are less than about 40% of the surface area of said roof, and said openings have a horizontal width to depth ratio of greater than about 6:1.

5. The system of claim 1 wherein said roof is in a horizontal plane.

6. The system of claim 1 wherein roof is formed of a plurality of horizontal tiered portions each interconnected by an impermeable vertical portion.

7. The system of claim 2 wherein said roof is formed of a first array of parallel members, and a second array of parallel members perpendicularly intersecting said first array.

8. The system of claim 1 wherein said roof is formed of netting.

9. The system of claim 1 wherein said vapor absorbing means comprises a plurality of ports for generating a curtain of absorbing liquid and/or powder.

10. The system of claim 9 wherein said vapor absorbing means further comprises solid and/or semi-solid absorbent materials in said walled surfaces.

11. The system of claim 1 wherein said vapor absorbing means comprises solid and/or semi-solid absorbent materials in said walled surfaces, said absorbent materials being metal oxides, metal carbonates or metal hydroxides.

12. The system of claim 1 further comprising a tower extending upwardly through said roof, and means for generating a flow of air from said enclosure upwardly through said tower to remove said vapor from the air flow.

13. The system of claim 12 further comprising a spray in said tower for removing said vapor.

14. The system of claim 12 further comprising baffles in said tower for deflecting air flow, and absorbent material on said baffles for removing said vapor.

15. The system of claim 1 wherein said walled surfaces are substantially impermeable to said vapor.

16. A method for containment of heavy vapor cloud and aerosol from a potential source of hazardous vapor comprising the steps of:

surrounding said vapor source with walled surfaces;

positioning a roof above said vapor source to form with said walled surfaces an enclosure for said vapor source, said roof being porous with openings therethrough extending over at least about 20% of the surface area of said roof to provide access for ambient light, air and precipitation, said openings being dimensioned for minimizing wind shear and resultant wind shear eddies within said enclosure by interrupting transmission of momentum from ambient air to air within said enclosure, and locating within said enclosure means for absorbing said vapor;

whereby said roof increases residence time of said vapor with said absorbing means.

17. The method of claim 16 wherein said openings in said roof are greater than about 40% of the surface area of said roof, and said openings have a horizontal width to depth ratio of less than about 6:1.

18. The method of claim 17 wherein said horizontal width to depth ratio of said openings is less than about 3:1.

19. The method of claim 16 wherein said openings in said roof are less than about 40% of the surface area of said roof, and said openings have a horizontal width to depth ratio of greater than about 6:1.

20. A system for containment of heavy vapor cloud and aerosol from a potential source of hazardous vapor comprising:

a potential hazardous vapor source; walled surfaces surrounding said vapor source;

a roof above said vapor source and forming with said walled surfaces an enclosure for said vapor source, said roof being formed of netting with openings therethrough dimensioned for minimizing wind shear, said openings extending over greater than about 40% of the surface area of said roof and having a horizontal width to depth ratio of less than about 6:1; and means within said enclosure for absorbing said vapor.

* * * * *